United States Patent [19]
Lum et al.

[11] Patent Number: 5,932,315
[45] Date of Patent: Aug. 3, 1999

[54] MICROFLUIDIC STRUCTURE ASSEMBLY WITH MATING MICROFEATURES

[75] Inventors: Paul Lum; Michael Greenstein, both of Los Altos, Calif.

[73] Assignee: Hewlett-Packard Company, Palo Alto, Calif.

[21] Appl. No.: 08/846,570

[22] Filed: Apr. 30, 1997

[51] Int. Cl.$^6$ ............................... B32B 3/00; B28B 5/00; B01D 47/00

[52] U.S. Cl. ........................ 428/172; 428/156; 428/167; 428/178; 428/188; 264/138; 264/220; 264/241; 156/292; 156/244.19; 156/297; 156/308.4; 261/110

[58] Field of Search .................................. 428/156, 167, 428/172, 192, 212, 178, 188, 120; 264/138, 241, 166, 167, 297.1, 220, 250, 299; 261/108, 110; 210/151, 294, 322; 156/290, 292, 308.4, 244.19, 250, 297

[56] References Cited

U.S. PATENT DOCUMENTS

| | | | |
|---|---|---|---|
| 4,668,607 | 5/1987 | Wojcik | 430/281 |
| 4,891,120 | 1/1990 | Sethi et al. | 104/299 |
| 4,908,112 | 3/1990 | Pace | 204/299 |
| 5,132,012 | 7/1992 | Miura et al. | 210/198.2 |
| 5,194,133 | 3/1993 | Clark et al. | 204/299 |
| 5,443,890 | 8/1995 | Ohman | 428/167 |
| 5,500,071 | 3/1996 | Kaltenbach et al. | 156/272.8 |
| 5,534,328 | 7/1996 | Ashmead | 428/166 |
| 5,571,410 | 11/1996 | Swedberg et al. | 210/198.2 |

OTHER PUBLICATIONS

Fan et al., "Micromachining of Capillary Electrophoresis Injectors and Separators on Glass Chips and Evaluation of Flow at Capillary Intersections", 1994, vol. 66(1), pp. 177–184, Anal. Chem.

Manz et al., "Planar Chips Technology for Miniaturization of Separation Systems: A Developing Perspective in Chemical Monitoring", 1993, vol. 33, pp. 1–67, Advances in Chomatography.

Harrison et al., "Towards Miniaturized Electrophoresis and Chemical Analysis Systems on Silicon: An Alternative to Chemical Sensors", 1993, vol. B(10), pp. 107–116, Sensors and Actuators.

Manz et al., "Micromachining of Monocrystalline Silicon and Glass for Chemical Analysis Systems . . . ", vol. 10(5), pp. 144–149, Trends in Analytical Chemistry.

DuPont Electronics, "Pyralin PD Polymide Coatings PI–2700 Processing guidelines", 1991, pp. 1–12.

Manz et al., "Design of an Open–Tubular Column Liquid Chromatography Using Silicon Chip Technology", 1990, vol. B(1), pp. 249–255, Sensors and Actuators.

Becker et al., "Fabrication of Microstructures with High Aspect Ratios and Great Structural Heights by Synchrotron Radiation Lithography, Galvanoforning, and Plastic Moulding (LIGA Process)", 1986, pp. 35–56, Microelectronic Engineering (North–Holland).

Bean, "Anisotropic Etching of Silicon", 1978, vol. ED–25(10), pp. 1185–1193, IEEE Transactions on Electron Devices.

Declercq, "A New C–MOS Technology Using Anisotropic Etching of Silicon", 1975, vol. SC–10(4), pp. 191–1196, IEEE Journal of Solid–State Circuits.

(List continued on next page.)

*Primary Examiner*—Donald Loney
*Attorney, Agent, or Firm*—Philip S. Yip

[57] ABSTRACT

A microfluidic structure assembly having a microchannel formed by bonding two plates together is disclosed. The microfluidic structure assembly includes a first plate and a second plate. At least one of these plates has one or more microgrooves. Microdepressions and microprojections are also present in the plates and they connect such that the microprojections of one plate fit into the microdepressions of the other plate. As a result, the two plates are proximate to each other to form an assembly in which the microgrooves to form microchannels. These microdepressions and microprojections securely lock the microchannels into desired positions. Preferably the plates are made by molding to form the microdepressions, microgrooves, and microchannels.

22 Claims, 8 Drawing Sheets

OTHER PUBLICATIONS

Tenney et al., "Etch Rates of Doped Oxides in Solutions of Buffered HF", 1975, vol. 120(8), pp. 1091–1095, J. Electrohem. soc.: Solid State Science and Technology.

Theunissen et al., "Application of Preferential Electrochemical Etching of Silicon to Semiconductor Device Technology", vol. 1970, 117(7), pp. 959–965, ,J. Electrohem. soc.

Robbins et al., "Chemical Etching of Silicon, II", 1960, vol. 107(2), pp. 108–111,J. Electrohem.soc.

Robbins et al., "Chemical Etching of Silicon, I", 1959, vol. 106(6), pp. 505–508,J. Electrohem.soc.

MICROFLUIDIC STRUCTURE ASSEMBLY WITH MATING MICROFEATURES

FIELD OF THE INVENTION

The present invention relates to a miniaturized device with small capillaries, more particularly, to a miniaturized device and a method of making such a device having small capillaries that can be manufactured relatively easily in mass production.

BACKGROUND

In liquid sample analysis, for example, in liquid chromatography, capillary electrophoresis, and blood chemistry analysis, smaller dimensions of capillaries will often result in improved performance characteristics, save time, and result in reduced production and analysis costs. Miniaturized channel or capillary systems provide more effective system design, result in lower overhead due to decreased instrumentation sizing and additionally reduce sample and solvent consumption.

An evolving approach for making capillaries that are useful for chemical analysis is by micromachining. Production of miniaturized separation systems involving fabrication of microstructures in silicon by micromachining or microlithographic techniques has been described. See, e.g. Fan et al., *Anal. Chem.* 66(1):177–184 (1994); Manz et al., *Adv. in Chrom.* 33:1–66 (1993); Harrison et al., *Sens. Actuators*, BB10(2):107–116 (1993); Manz et al., *Trends Anal. Chem.* 10(5): 144–149 (1991); and Manz et al., *Sensors and Actuators* B (Chemical) B1(1–6):249–255 (1990). The use of micromachining techniques to fabricate miniaturized separation devices on silicon or borosilicate glass chips can be found, in U.S. Pat. No. 5,194,133 (Clark et al.); U.S. Pat. No. 5,132,012 (Miura et al.); in U.S. Pat. No. 4,908,112 (Pace); and in U.S. Pat. No. 4,891,120 (Sethi et al). Miniaturized columns made in a polyimide material is disclosed in U.S. Pat. No. 5,500,071 by Kaltenbach et al. and in U.S. Pat. No. 5,571,410 by Swedberg et al. However, a need still exists for a technique that can manufacture in a relatively short time a large number of miniaturized channels or columns with well defined lumen.

SUMMARY

The present invention provides a microfluidic structure assembly and a technique for making the microfluidic structure assembly. The technique is well suited for making a large number of microfluidic structure assemblies efficiently. The microfluidic structure assembly is made by two plates securely coupled together by microprojections in one plate mating with microdepressions in the other plate.

Briefly stated, an embodiment of the microfluidic structure assembly includes a first plate and a second plate defining a microchannel. The first plate includes one or more microgrooves. The first plate has a mating side for mating with the second plate, as well has many microdepressions or microprojections, or both, on the mating side. The second plate also has a mating side, which has microdepressions or microprojections, or both, to enable the two plates to couple. The microprojections of one plate fit into the microdepressions of the other plate such that the mating sides of the two plates are proximate to each other to form an assembly. As a result, the microgrooves form microchannels. Microfluidic structures that can be incorporated in the assemblies include access ports, flow structures, processing structures, analysis structures, and assembly alignment structures.

Preferably, the first and second plates with microdepressions, microgrooves, microchannels, or the like are made by molding. As used herein, "molding" refers to solidifying a liquid in a confining structure (called a "mold" herein) with void areas such that the liquid, after solidifying into solid, would have its dimensions corresponding to the dimensions of the voids in the confining structure. Thus, "molding" herein includes casting a liquid in the tray-like confining structure open on top and allowing the liquid to solidify. In a preferred mode, a mold can be used to make a large plate having a large number of microfluidic structures such that the large plate can be divided into smaller pieces each having a similar microfluidic structure, e.g., a microgroove. In this way, by assembling two large plates matingly together and dividing that assembly, a large number of microfluidic structure assemblies can be manufactured in a relatively short time.

The technique of making microfluidic structure assemblies of the present invention can be used advantageously to make a large number of identical microfluidic structure assemblies with well-defined channels. The technique is particularly well suited for mass producing the microfluidic structure assemblies. Additionally, the microprojection-in-microdepression mating allows the two plates to be aligned and secured easily. Furthermore, by designing the plates such that a sufficient number of microdepressions and microprojections are proximate to and along the length the microgrooves, the exact position, dimension, and shape of the microchannels can be well controlled. This is particularly important when the two plates each have a microgroove such that they need to match precisely to form a microchannel of uniform cross-sectional size and shape. In a manufacturing process in which two plates need to be pressed together to bond, the position of the microchannel may change because of the pressure. The "tongue in groove" type of locking of the microprojections and microdepressions prevents the shifting of one plate relative to the other to maintain the shape and dimensions of the microchannels.

BRIEF DESCRIPTION OF THE DRAWING

The following figures, which show the exemplary embodiments of the present invention, are included to better illustrate the microfluidic structure assemblies of the present invention. In these figures, like numerals represent like features in the several views.

DETAILED DESCRIPTION

The present disclosures provides a technique for making a microfluidic structure assembly with two plates. In an embodiment of the microfluidic structure assembly, a plurality of microdepressions (or microwells) and a plurality of microprojections (or microtongues) are present in the two plates such that they can be mated together to secure the relative position of the plates. In at least one of the two plates are one or more microgrooves such that when the two plates are mated together, at least one microchannel is formed from the microgrooves. The two plates are preferably made by molding. Furthermore, a mold can be made such that many identical plates can be made from each mold, such that a large number of identical microfluidic structure assemblies can be made with two molds.

Figure 1A:
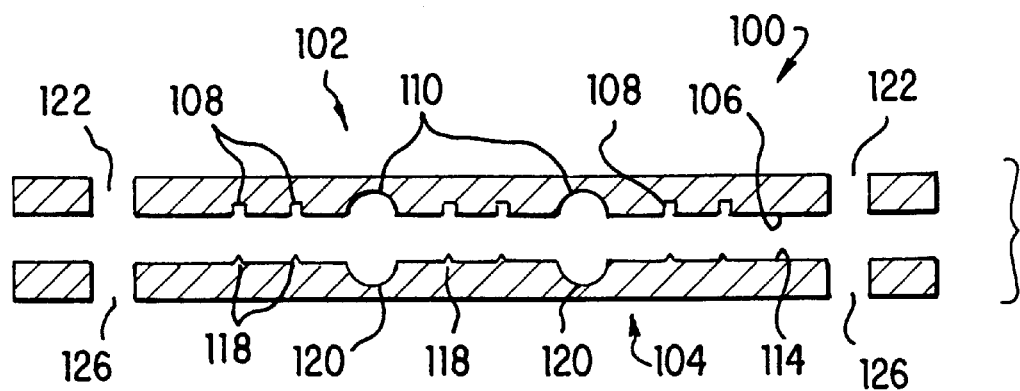
FIG. 1A shows an exploded sectional view of a microfluidic structure assembly of the present invention.
Figure 1B:
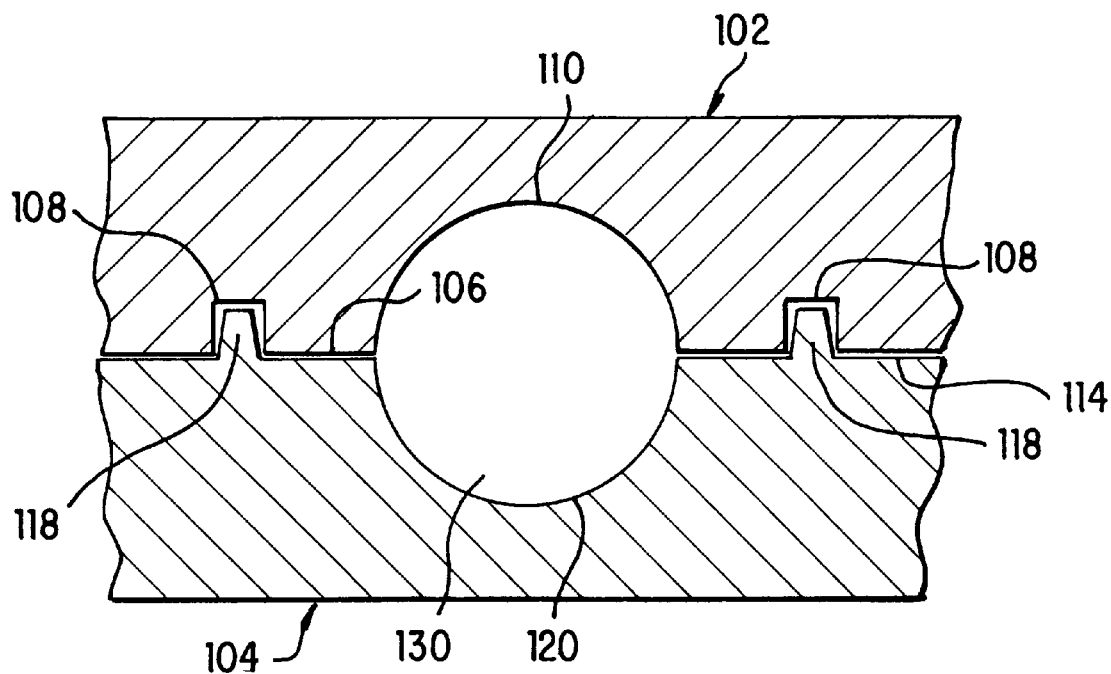
FIG. 1B shows a sectional view in portion of a microfluidic structure assembly of the present invention.

FIG. 1A and FIG. 1B illustrate an embodiment of the present invention.

FIG. 1A shows an exploded view of a microfluidic structure assembly of the present invention. The microfluidic structure assembly 100 includes a first plate 102 and a second plate 104. On the mating side 106 of the first plate 102 are a plurality of microdepressions 108. The mating side 106 of the first plate 102 also has at least one microgroove 110. Correspondingly, the mating side 114 of the second plate 104 has a plurality of microprojections 118. The same mating side 114 of the second plate 104 also has one or more microgrooves 120 corresponding to the microgrooves 110 of the first plate 102. Throughholes 122, penetrating through the thickness of the first plate 102, are located proximate to the edges of the first plate 102. Similarly, throughholes 126 are present penetrating through the thickness of the second plate 104 such that when the two plates 102 and 104 are mated together, the throughholes 122 and 126 couple to form longer throughholes that extend through the combined thickness of the two plates. These throughholes are useful for aligning the first and second plates for coupling such that the microdepressions and microprojections are proximate to mate with each other and the microgrooves 110 and 120 match each other.

FIG. 1B shows, in portion, a cross-sectional view of the microchannel 100. When the two plates 102 and 104 are coupled together, the microprojections 118 fit inside the microdepressions 108 such that the surface of the mating side 106 of the first plate 102 and the surface of the mating side 114 of the second plate 104 are in contact, except for any adhesive that is interposed between them. The microgrooves 110 of the first plate 102 are matched to the microgrooves 120 of the second plate 104 such that the microgrooves of the two plates combine to form a microchannel 130. As a result, the cross-section of the microchannel 130 is the sum of the cross-section of the microgroove 110 and the microgroove 120. It is also contemplated that only one of the plates 102, 104 can have a microgroove, in which case when the plates are coupled together, the microchannel has about the same dimensions as the microgroove.

The microchannel 130 is suitable for the conduction of fluid. The microdepressions 108 and the microprojections 118 facilitate the anchoring of the two plates 102 and 104 together, such that the microgrooves 110 and 120 are aligned accurately. For this reason, it is preferred that the cross-sectional areas of the microdepressions 108 are substantially smaller than the cross-sectional areas of the microgrooves 110 and 120. For example, the cross-sectional areas of the microgrooves 110, or microgrooves 120, may be ten or more times larger than those of the microdepressions 108. It is contemplated that the plates, i.e., the first plate 102, and the second plate 104, each may contain both microdepressions 108 and microprojections 118. It is noted that the microprojections and microdepressions of the present invention are different from conventional throughholes typically used for roughly aligning separate pieces of structures together. Preferably, the microprojections and microdepressions are positioned such that a least some of them are close to and along the microchannels to align the microgrooves to form microchannels such that the position and dimensions of the microchannels are well defined and controlled.

Figure 2:
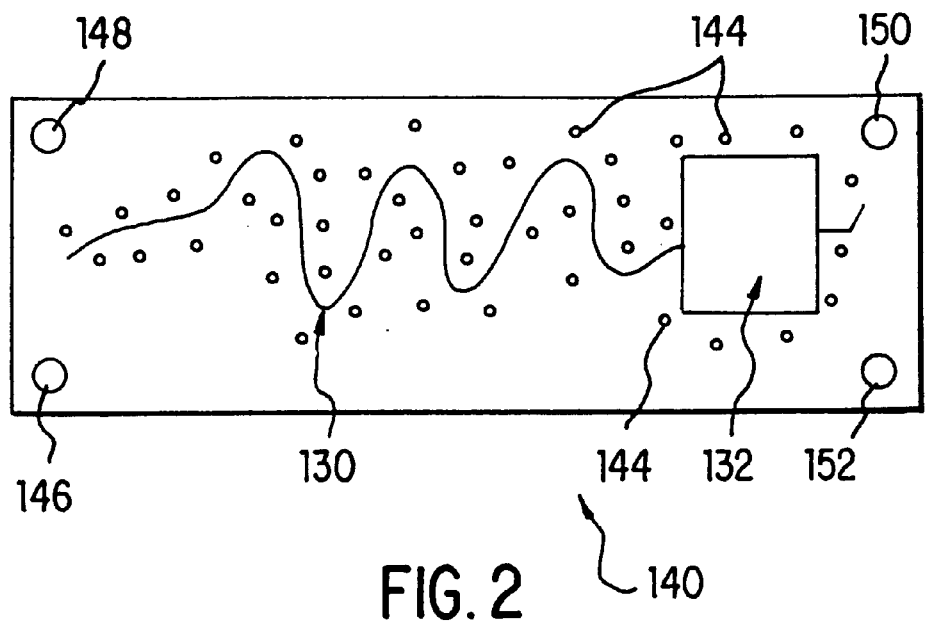
FIG. 2 shows a plan view of an embodiment of a microfluidic structure assembly according to the present invention.

FIG. 2 shows a plan view of an embodiment of a microfluidic structure assembly according to the present invention. The microfluidic structure assembly 140 includes a microchannel 130, which is connected to and in fluid communication with a chamber 132, both of which are formed by two plates mating together. Microanchors 144 containing microdepressions and microprojections (not shown in FIG. 2) are scattered throughout the two plates such that they can be mated to anchor the plates together securely. Preferably, some of the microanchors 144 are distributed along both sides of the microchannel 130 and around the chamber 132, such that the course of the microchannel 130 and the inside walls of the chamber 132 are well defined with minimal mismatch between the two plates.

When the two plates are mated together, throughholes 146, 148, 150, and 152 are present at the four corners of the microfluidic structure assembly 140, such that the two plates can be aligned before they are mated. In application, using the throughholes, e.g., by extending rods through them, provides a rough alignment between the two plates such that the microdepressions on one plate is proximate to the microprojections of the other plate. Then one may move one plate relative to the other until the microprojections partially insert into the microdepressions. By pressing the plates together, one can lock the plates together to define firmly the microchannel and chambers, and the like, to close tolerance between the two plates.

Such a microfluidic structure assembly can be used for a variety of applications. For example, the microchannel 130 can have an opening to a space external to the microfluidic structure assembly such that a fluid can be conducted through the opening to the microchannel. The chamber 132 can contain a chemical reagent that reacts with the fluid conducted through microchannel 130 from the opening. In this way, the properties of a particular fluid can be examined. One application contemplated is to have in the chamber 132 a chemical reagent that reacts with certain components of blood, e.g., to indicate the concentration of hemoglobin, glucose, other chemicals in the blood, and the like. Of course, other liquid samples can be analyzed in a similar manner. Further, a liquid, once conducted to a chamber, can also be analyzed optically for a variety of characteristics, such as by light absorption, transmission, scattering, spectral analysis, etc. There can also be more than one chambers, each of which performing a separate function. For example, one chamber can be a fluid handling chamber, e.g., for storage if fluid; one can be a fluid processing or reaction chamber; and one can be an analysis chamber. It is further contemplated that microfluidic valves, pumps, and the like be included in the assembly.

METHOD OF MAKING A MCROFLUIDIC STRUCTURE ASSEMBLY

Although the microfluidic structure assembly of the present invention can be made by conventional processes to cut or etch out one microgroove on one plate at a time, the preferred way of making the microfluidic structure assembly of the present invention is by molding the two plates of the microfluidic structure assembly. In this way, a large number of microfluidic structure assemblies can be made in a relatively short period of time.

Figure 3:
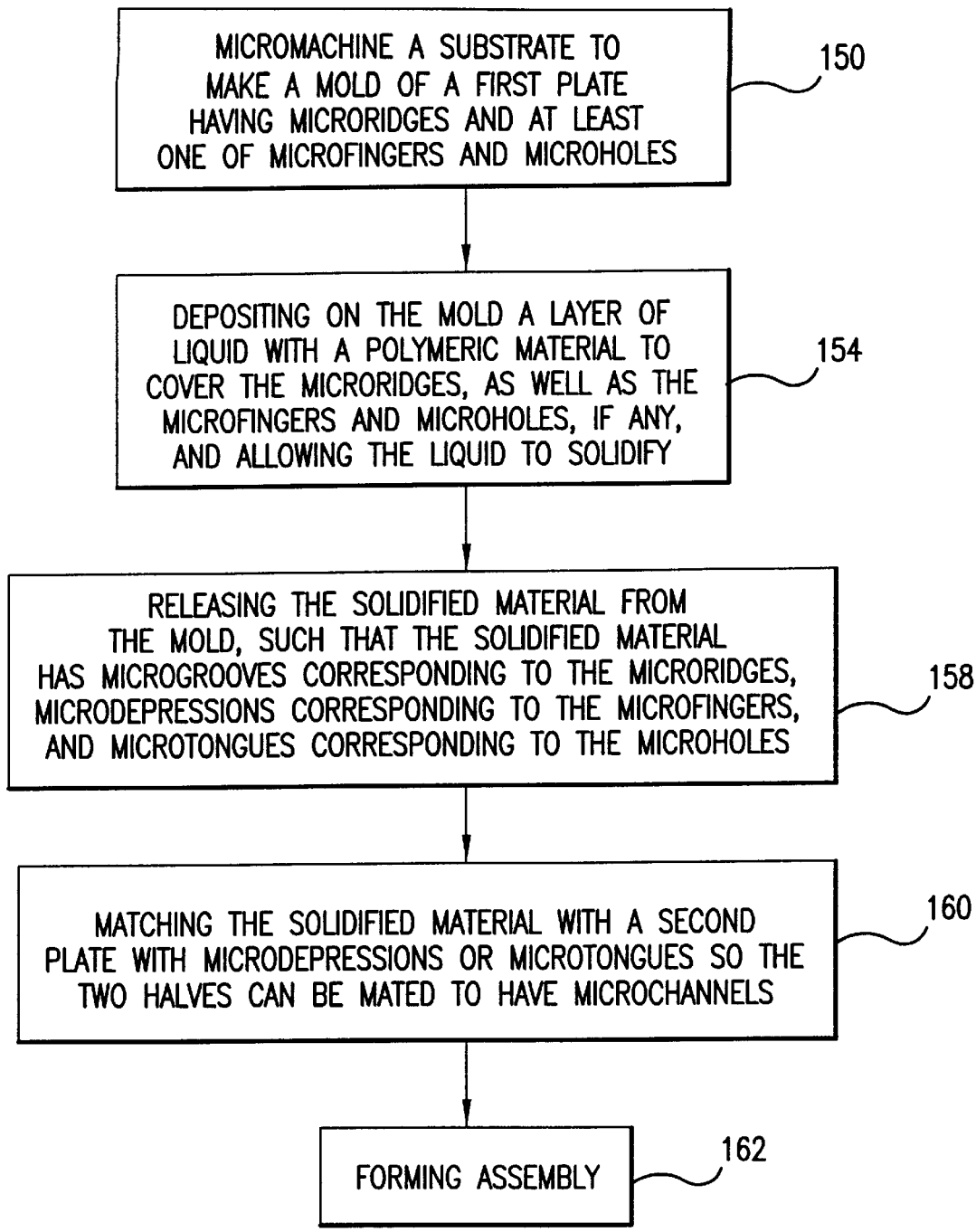
FIG. 3. shows a flow chart outlining a process for making the microfluidic structure assemblies.

FIG. 3. shows an outline used for a process of making the microfluidic structure assemblies of the present invention. In this process, a substrate is micromachined to form a mold (i.e., a template plate) for a plate (e.g., the first plate) of a microfluidic structure assembly. This can be done to obtain molds for both the first plates and the second plates of the microfluidic structure assemblies. For example, depending on the design of the microfluidic structure assembly, the mold for the first plate can have one or more of microridges and a plurality or microfingers or microholes, or both (block 150 in FIG. 3). A layer of liquid for forming a polymeric material is deposited on the mold (e.g., for the first plate) to cover the microridges, as well as the microfingers and microholes if they are present. The liquid is then allowed to solidify to form a solidified, molded plate (block 154). The molded plate is then released from the mold. In the molded plate are microgrooves corresponding to the microridges, microdepressions corresponding to the microfingers, and microprojections corresponding to the microholes, depending on whether it is desired for them to be on one or both plates of the microfluidic structure assembly (block 158). However, at least one of the plates will have the microgroove, and at least one of the plates will have microdepressions whereas the other plate will have the corresponding microprojections. The first plate is then bonded with a second plate in a way that the two plates can be mated together, with the microprojections mating with the microdepressions on the two plates. Preferably, microgrooves are present in the two plates to combine into microchannels (block 160). As a result, a microfluidic structure assembly of the present invention is formed (block 162).

As an illustration, a process for forming a microfluidic structure assembly will be described below, in which a first plate has only microdepressions and a second plate has only microprojections for fitting into the microdepressions of the first plate. The first and second plates are made by a modeling technique.

Figure 4A:
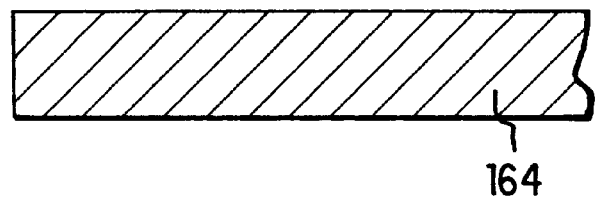
FIG. 4A shows a sectional view of a substrate for making a mold.

A thin plate of substrate (shown in FIG. 4A) 164 is micromachined on one side to produce a plurality of microfingers 166 and one or more microridges 168. The substrate 164 can be made of a material that is solid and compatible with the liquid with polymers for making the plates of the microchannels assembly. For example, the substrate may be made of metal, e.g., stainless steel, copper, a polymeric material, and the like. Preferably the substrate is made of silicon. Depending on the material of construction the substrate can be micromachined with a mechanical process or a chemical etching process, or both. For example, a metallic substrate such as a stainless steel sheet can be micromachined using microsaws, drills, and the like. A silicon substrate can be chemically etched by employing suitable etchants, such as potassium hydroxide (KOH), tetramethyl ammonium hydroxide (TMAH), hydrofluoric acid (HF), and the like.

Figure 4B:
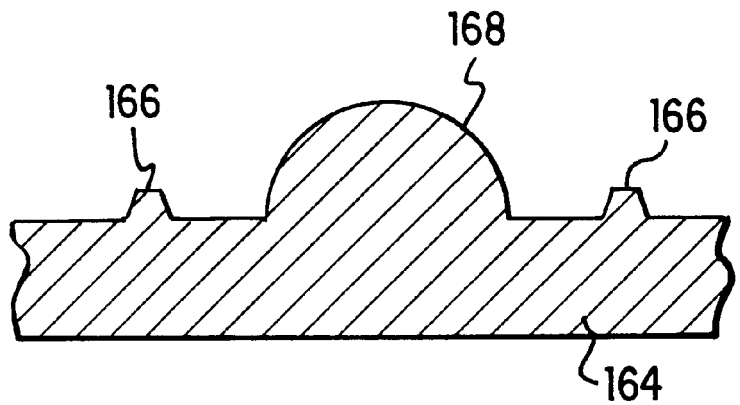
FIG. 4B shows a mold made from the substrate of FIG. 4A.
Figure 4C:
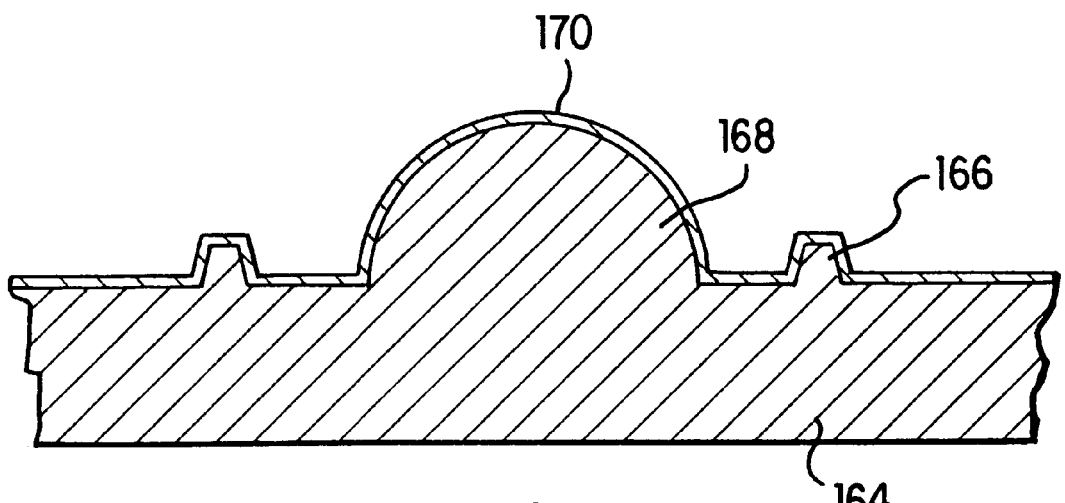
FIG. 4C shows the sectional view of the mold having a release layer on the mode.
Figure 4D:
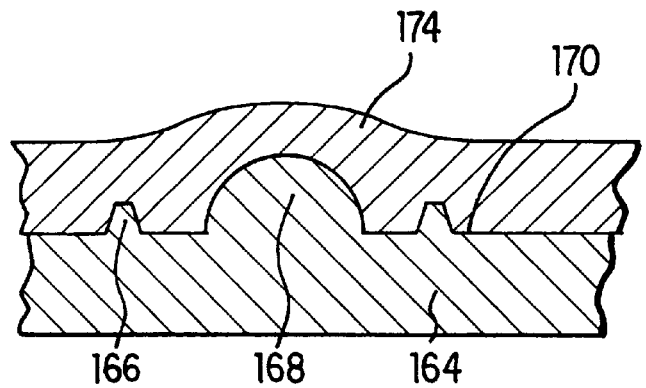
FIG. 4D shows the sectional view of the mold having a liquid disposed on the mold.

Methods for photolithographic processes are known in the art. As an example, a layer of photoresist can be deposited on the substrate and a desired pattern of areas to be etched can be photoimaged on the photoresist. The unwanted area on the photoresist is removed and a suitable etchant is then employed to etch the substrate. In this way, the substrate 164 can be shaped to have microridges 168 and microfingers 166 of selected thicknesses and heights (FIG. 4B). A layer 170 of a release material, if desired, is deposited or formed on the surface of the side of the substrate having the microfingers 166 and microridges 168 (FIG. 4C). Subsequently, a liquid having a polymer-forming material, which can be a liquid with monomers that will polymerize, or with polymers that can further polymerize or coalesce to solidify, is deposited on top to the release material layer 170 on the substrate 164 (FIG. 4D). An example of such a liquid is one that contains prepolymeric material that would polymerize into a thermoset polymer, e.g., a polyimide. As an example, PYRALIN PD PI-2700 polyimide solution (DuPont) can be used. Further, a suitable solvent can be used to thin the liquid to a desired viscosity and for forming a solid with desired rigidity. In the case of the PYRALIN PD PI2700, thinners such as dimethyl sulfoxide may be used. Epoxy resins, polyesters and polyamides can also be used for forming the mating plates. Other polymers, either thermoset or thermoplastic, would be obvious to one skilled in the art of molding with polymeric materials.

Figure 4E:
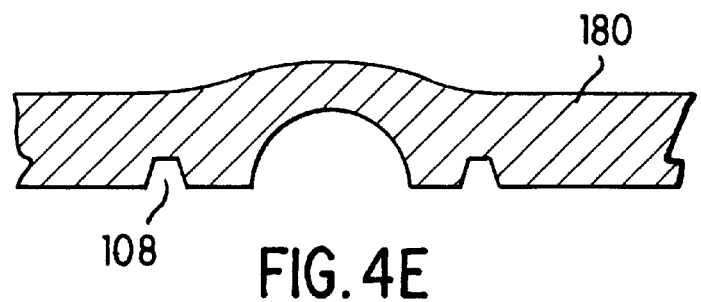
FIG. 4E shows the sectional view of a first plate of the microfluidic structure assembly formed from the mold of 4B.
Figure 4F:
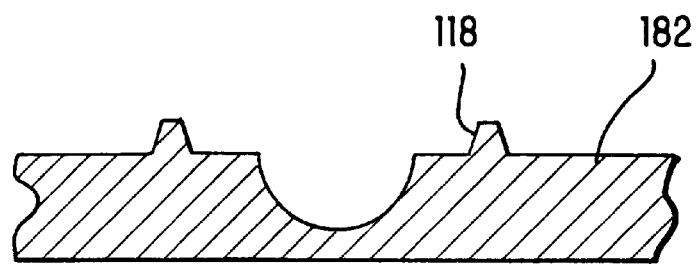
FIG. 4F shows the sectional view of a second plate that matches the first plate of the microfluidic structure assembly.

The deposition of the liquid can be facilitated by employing a vacuum to remove gas between the substrate 164 and the liquid layer 174 such that essentially all of the voids or bubbles are eliminated between the two (FIG. 4D). Further, spinning, as in centrifuging, can be used for urging the liquid containing polymeric material into any voids, depressions, or crevasses on the substrate 164. The liquid layer 174 is then allowed to solidify. This can be accomplished, for example, by applying heat to facilitate polymerization (as in the case of the PYRALIN PD PI-2700 example), and to evaporate any solvent or liquid reaction product after polymerization. Releasing the solidified layer 174 from the substrate 164 (FIG. 4E) results in a first plate 180. In the event that the top surface of the first plate 180 is not completely flat, the top side of the first plate 180 may be lapped to result in a flat surface. By a similar process, a second plate of the microfluidic structure assembly 182, having a plurality of microprojections 118, can be formed (FIG. 4F).

Figure 5:
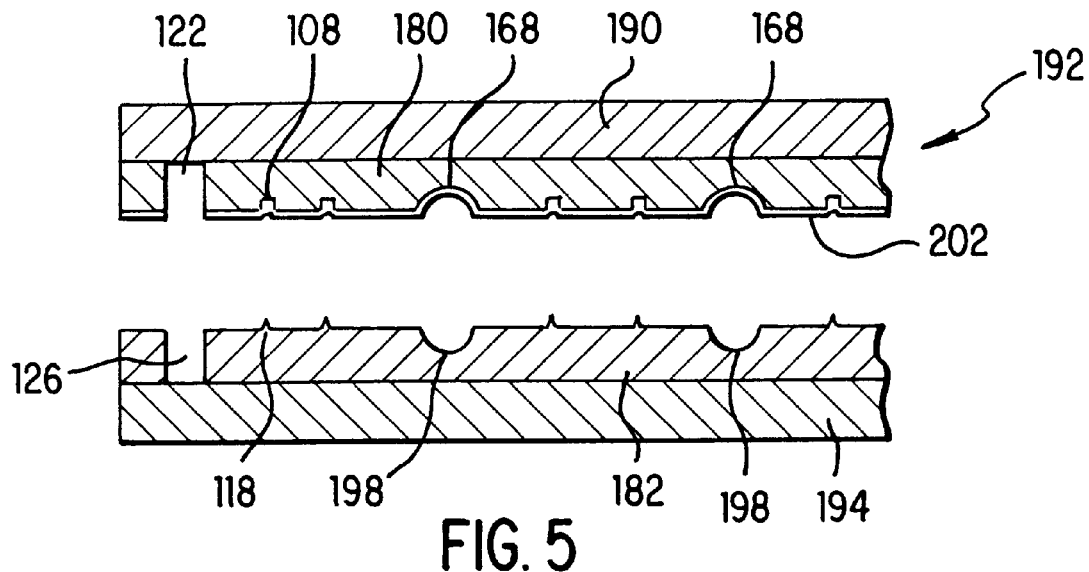
FIG. 5 shows how in sectional view the first and second plates of FIG. 4E and FIG. 4F being coupled together.

The two plates 180 and 182 of the microfluidic structure assembly, now having flat surfaces, can be coupled together to form the microfluidic structure assembly. FIG. 5 shows how this can be done. A first part 190 of an assembly holder 192 holds the first plate 180 of the microfluidic structure assembly. The second part 194 of the microfluidic structure assembly holder 192 holds the second plate 182 of the microfluidic structure assembly. The two plates 180 and 182 are held in the holder 192 such that the microdepressions 108 face the microprojections 118. When the two plates are brought together the microprojections 118 fit inside the microdepressions 108. The microgrooves 168 of the first plate of 190 match with the microgrooves 198 of the second plate 182 to form microchannels. A thin layer of a suitable adhesive 202 is deposited on the mating side of one (of both, if desired) of the plates 180 and 182 for adhering the two plates together. The two plates of the microfluidic structure assembly 180 and 182 are brought and pressed together so that the adhesive material is squeezed from the space between the microdepressions 108. Preferably, the adhesive is deposited thinly and in suitable location such that it will not be squeezed into the microchannel excessively to change substantially the microchannel's cross-sectional area or dimensions.

The two plates of the microfluidic structure assembly 180 and 182 are held together. The adhesive can be cured or annealed, for example, by applying heat to the adhesive, such that the two plates are securely bonded together. The heating can be done, for example, in an oven of 600° C. for a polyamide adhesive, e.g., KAPTON KJ adhesive by DuPont Co., Wilmington, Del.

Figure 6:
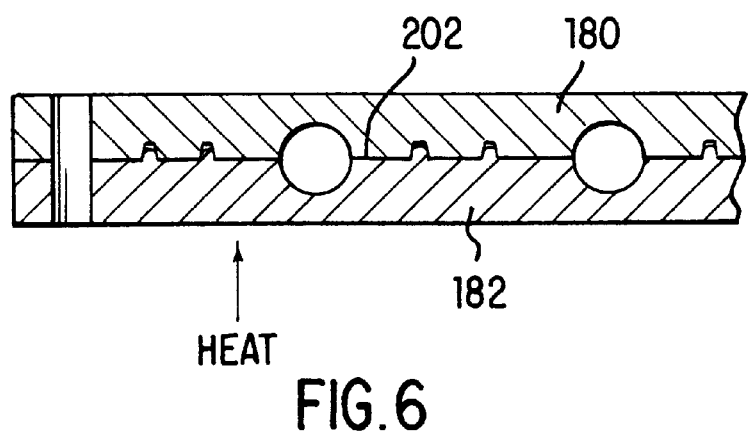
FIG. 6 shows in sectional view a microfluidic structure assembly formed by the coupling of the two plates of FIG. 5.

The throughholes 122 and 126 can be used for aligning the two plates 180 and 182 so that the microdepressions 108 face the microprojections 118, and the microgrooves 168 face the microgrooves 198. Furthermore, an imaging device can be used to view the two plates when the are proximate to each other before they are pressed together to ensure that they face each other in a correct position for mating. (FIG. 6).

Figure 7:
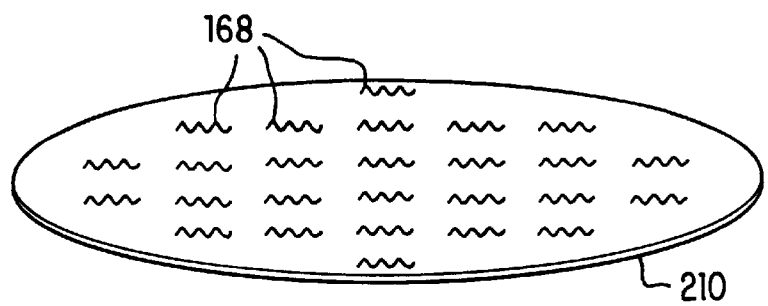
FIG. 7 shows in isometric view a wafer having a plurality of microgrooves.
Figure 8:
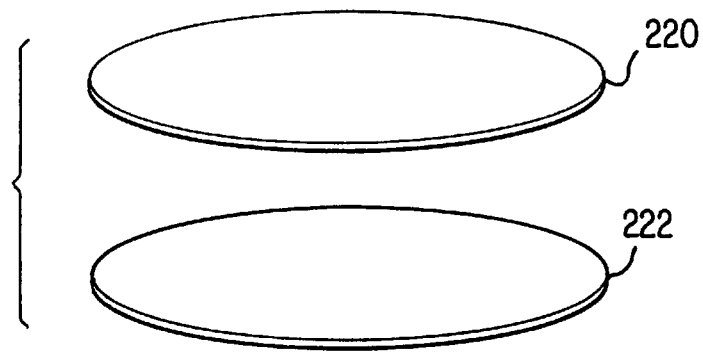
FIG. 8 shows in isometric view the coupling of two matching wafers.

Instead of making a single microfluidic structure assembly having one or a few microchannels, a plurality of microfluidic structure assemblies can be made by making a large microfluidic structure assembly having microchannels such that the large microfluidic structure assembly can be divided into pieces each having microchannels. Preferably, all the pieces from a large microfluidic structure assembly are identical to facilitate the manufacturing process. This is illustrated in FIG. 7. Although other substrates can be used, for illustration, a process using a substrate of silicon is described. A wafer of silicon 210 is micromachined to have a plurality of microridges, microfingers 118, microholes 108 with the techniques described earlier. (The microfingers 118 and the microholes are not shown in FIG. 7.) In this illustration, the microridges on a wafer are identical. A layer of liquid for forming a polymeric material is deposited on top of the micromachined silicon wafer 210 and allowed to solidify for molding. The solidified, molded, polymeric material is lapped to impart a flat surface. After releasing, a large thin molded plate (molded plate 220 of FIG. 8) is obtained, having a polarity of microgrooves corresponding to the microridges.

Figure 9:
FIG. 9 shows in isometric view a large microfluidic structure assembly containing a large number of microchannels.
Figure 10:
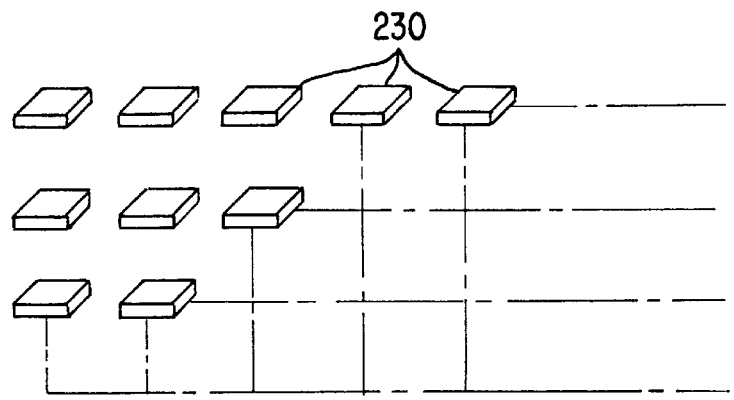
FIG. 10 shows in isometric view the division of a large microfluidic structure assembly into a plurality of smaller microfluidic structure assemblies each having a microchannel.
Figure 11:
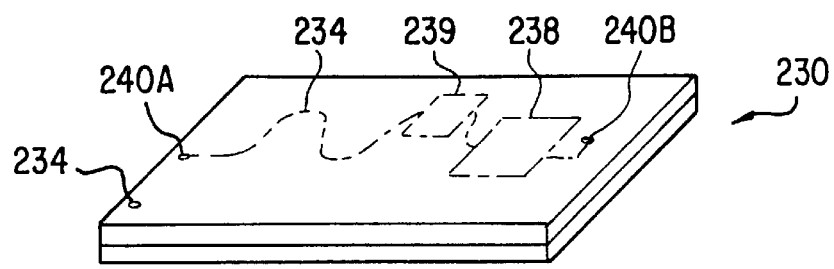
FIG. 11 shows in isometric view a small microfluidic structure assembly formed from a large microfluidic structure assembly of FIG. 10.

By a similar process, another large thin plate 222 (shown in FIG. 8) of solidified, molded polymeric material is made, having a plurality of microgrooves corresponding to the microgrooves in the other plate. The first molded plate 220 resulting from the substrate 210 and the second molded plate 222 can be mated together with an adhesive disposed therebetween as described earlier, similar to the process depicted in FIG. 5 and FIG. 6 to result in a large microfluidic structure assembly 226, which contains the first plate 220 and the second plate 222 (FIG. 9). The large microfluidic structure assembly 226 can then be divided into many identical microfluidic structure assemblies 230 (as shown in FIG. 10). In this embodiment, each of the microfluidic structure assemblies 230 has a microchannel 234 (FIG. 11). As described earlier, if desired, the microfluidic structure assembly similar to the microfluidic structure assembly 140 in FIG. 2 can also contain chambers 238, 239. Openings 240 A and 240 B may also be provided to connect the microchannel 234 to space exterior to the microfluidic structure assembly 230. Additionally, it is contemplated that other microcavities, microchannels, microtubes, etc., can also be present in the microfluidic structure assembly 230. Optionally, throughholes 234 can also be present in the microfluidic structure assembly. Such throughholes 234 can facilitate the alignment of the first plate 220 and the second plate 222 to form the microfluidic structure assembly 226 before dividing into sub-assemblies.

Figure 12A:
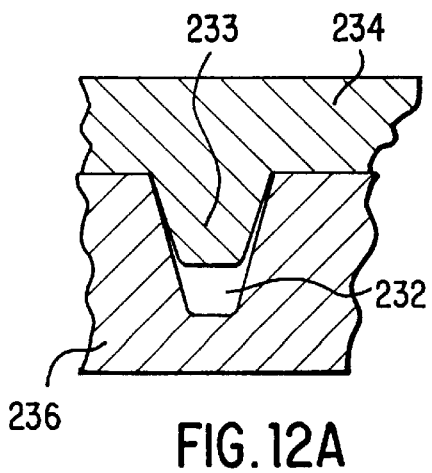
FIG. 12A shows a sectional view of a microprojection coupling with a microdepression.
Figure 12B:
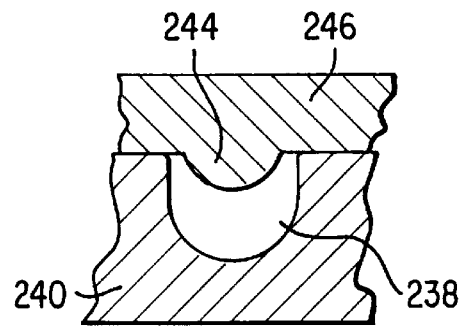
FIG. 12B shows a sectional view of another kind of microprojection coupling with a microdepression.

Depending on the application of the microfluidic structure assembly, the size, thickness, and other dimensional characteristics of the plates, as well as the size, shape, and other dimensional characteristics of the microchannel, chambers, microanchors, microdepressions, microprojections, and the like, can vary to adapt to the application. For example, as shown in FIG. 12 A, the microdepression 232 can be about the same size as the microprojection 233 so the two are tightly mated when the two plates 234, 236 are pressed together. In one alternative, as shown in FIG. 12B, the microdepression 238 in one plate 240 is somewhat smaller than the micro projection 244 of the other plate 246 so they can be fitted easily.

The dimension of the microchannel can vary depending on the application. For example, a blood chemistry analysis microfluidic structure assembly may have a microchannel with a diameter of about 50 $\mu$m to 500 $\mu$m, preferably about 75 $\mu$m to 200 $\mu$m if the microchannel has a circular cross-section, or a microchannel of equivalent size if the microchannel is not exactly circular in cross-section. The length of the microchannel can be varied to adapt to the desired application. For analysis of a fluid, e.g., body fluid, the microchannel length is preferably about 0.1 mm to 100 mm, more preferably about 1 mm to 20 mm. The plates will have a thickness adequate for maintaining the integrity of the microfluidic structure assembly. Microchannels for other applications, such as chromatography, may have other, typically longer, dimensions.

The molds, or template plates, for making the plates of the microfluidic structure assemblies can be made by chemical or mechanical techniques. Preferably, for substrates such as silicon, silicon dioxide, and the like, the molds can be made by adopting micromachining methods for semiconductors known in the art. Such techniques include, but are not limited to, dry etching, chemical etching, LIGA, and laser ablation.

For example, it is commonly known that glass and $SiO_2$ can be etched with suitable chemicals, e.g., buffered hydrofluoric acid (HF) mixtures; silicon can be etched with potassium hydroxide (KOH) or tetramethyl ammonium hydroxide (TMAH); glass, $SiO_2$, polysilicon, and silicon nitride can be dry-etched with plasma chemistry known to one skilled in the art; and silicon nitride can also be wet-etched with phosphoric acid ($H_3PO_4$). Silicon, $SiO_2$, polymeric plates such as polyimide plates can be micromachined to form grooves by laser-ablation. It is also known that etchants such as KOH etch silicon anisotropically whereas etchants such as TMAH etch silicon isotropically. Thus, depending on the shape to be etched, different etchants can be used. As an example, a silicon layer can be lithographically masked and patterned with KOH or TMAH. Hot $H_3PO_4$ at about 50° C. can be used to etch silicon nitride. Other than using a suitable agent to chemically removing the lithographic masking material on top of the layer to be etched, the lithographic masking material can be removed by an oxygen plasma with minimal effect on the underlying layer. $SiO_2$ can be etched with, e.g., a dilute (say 10:1) hydrofluoric acid to remove the exposed $SiO_2$.

Chemical etching is a useful way of forming microstructures on a substrate and such techniques are known in the art. For example, a layer of photosensitive polymer (e.g., polyimide) can be covered with a mask and exposed to UV light to cross-link the polymer. The layer is then etched with a suitable chemical to removed polymer from selected areas according to the pattern of the mask. This results in structures such as channels and depressions on the layer. An example of a dry technique for etching polymers is a plasma based process. In this process, a mask is layered over a polymeric layer and ionized gases is directed to the polymeric layer to erode the area not covered by the mask. Etching techniques, including wet or dry processes, for polymeric substances are described, for example, in Frazier, A. B., et al., *Sensors and Actuators* A, 45: 47–55 (1994) and references cited therein. Methods for etching silicon dioxide are described in Steinbruchel et al., "Mechanism of dry etching of silicon dioxide—A case study of direct reactive ion etching," *J. Electrochem. Soc. Solid-state and Technology*, 132(1), pp. 180–186, January 1985; and Tenney et al., "Etch Rates of Doped Oxide in Solutions of Buffered HF," *J. Electrochem. Soc. Solid State and Technology*, 120 (8), pp. 1091–1095, August 1973. Polysilicon etching is described by Bergeron et al., "Controlled Anisotropic Etching of Polysilicon," *Solid State Technologies*, August 1982, pp. 98–103; and B. L. Sopori, "A New Defect Etch for Polycrystalline Silicon," *J. Electrochem. Soc. Solid State and Technology*, 131 (3), pp. 667–672, March 1984. Silicon nitride etching is described by van Gelder et al., "The etching of Silicon Nitride in Phosphoric Acid with Silicon Dioxide as a mask", *J. Electrochem. Soc. Solid State and Technology*, 114 (8), August 1967, pp. 869–872. Silicon etching is described by M. J. Declercq, "A New CMOS Technology Using Anisotropic Etching of Silicon," *IEEE J. of Solid State Circuits*, Vol. SC-10, No. 4, August 1975, pp. 191–196; K. E. Bean, "Anisotropic Etching of Silicon," *IEEE Trans. Electron. Devices*, Vol. ED-25, No. 10, October 1978, pp. 1185–1193; Osamu Tabata, "pH-controlled TMAH etchants for silicon micromachining," *Sensors and Actuators*, A53, 1996, pp. 335–339, Robbins, et al., "Chemical Etching of Silicon II. The system of HF, $HNO_3$, $H_2O$, and $HC_2H_3OO_2$," *J. Of The Electrochemical Society*, 107 (2), February 1960, pp. 108–111; K. R. Williams et al., "Etching for micromachining processing," *Memorandum N. UCB/ERL M96/37*, Jun. 18, 1996, Electronics Research Laboratory, College of Engineering, UC Berkeley; M. J. J. Theunissen et al., "Application of Preferential electrochemical etching of silicon to semiconductor device technology," *J. Electrochemical soc.*, July 1970, pp. 959–965; and A. S. Tenney et al., "Etch rates of doped oxides in solutions of buffered HF," *J. Electrochem. Soc.: Solid State Science and Technology*, 120(8), August 1973, pp 1091–1095. These etching methods are incorporated by reference herein.

For glass, quartz, silicon, and silicon dioxide substrates, etching techniques are also practicable. Generally, such a technique involves steps of masking and etching with chemical. For example, a silicon substrate is first covered with a coating of silicon dioxide by thermal oxide deposition and then further coated with a photoresist. The photoresist is then masked and exposed to light of suitable wavelength by photolithography. By developing the photoresist, selected areas of the silicon dioxide is exposed. This exposed area is then etched chemically to remove the silicon dioxide, thus exposing a selected area of the silicon. This exposed silicon area can then be chemically etched to form grooves, depressions, and the like. Along the way, the photoresist and the silicon dioxide coatings can be removed. By using analogous methods, glass and silicon dioxide substrates can be masked and etched to result in microstructures on a substrate. Examples of such techniques can be found in, for example, Fan, Z. H., et al., *Anal Chem.*, 66(1): 177–184 (1994), Manz et al., *Adv. in Chrom.* 33:1–66(1993), and Manz et al., *Trends Anal. Chem.* 10(5):144–149(1991).

The LIGA process is a process for fabricating microstructures having high aspect ratios and increased structural precision using synchrotron radiation lithography, galvanoforming, and plastic molding. Under a LIGA process, radiation sensitive plastics are lithographically irradiated at high energy radiation using a synchrotron source to create desired microstructures (such as channels, ports, apertures and micro-alignment means), thereby forming a primary template. The primary template is then filled with a metal by electrodeposition techniques. The metal structure thus formed comprises a mold insert for the fabrication of secondary plastic templates which take the place of the primary template. In this manner, highly accurate replicas of the original microstructures may be formed in a variety of substrates by solidifying a molding (e.g., polymeric) liquid in the mold. This includes using injection or reactive injection molding techniques. The LIGA process has been described by Becker, E. W., et al., *Microelectric Engineering* 4 (1986) pp. 35–56. Descriptions of numerous polymer substrates which may be injection molded using LIGA templates, and which are suitable substrates in the practice of the present invention, may be found in "Contemporary Polymer Chemistry", Allcock, H. R. and Lampe, F. W. (Prentice-Hall, Inc.) New Jersey (1981).

A technique that is suitable for forming microstructures for a microchannel mold of the present invention is laser ablation. The term "laser ablation" is used to refer to a machining process using a high-energy photon laser such as an excimer laser to ablate features in a suitable substrate. Laser ablation is described by Znotins, T. A., et al., *Laser Focus Electro Optics*, (1987) pp. 54–70; U.S. Pat. Nos. 5,291,226 and 5,305,015 to Schantz et al.; U.S. Pat. No. 5,500,071 and U.S. Pat. No. 5,571,410 to Swedberg et al. The above descriptions on forming microstructures using etching, LIGA, or laser ablation are incorporated by reference herein.

Although the illustrative embodiments of the microfluidic structure assemblies of the present invention and the method of making and using the microfluidic structure assemblies have been described in detail, it is to be understood that the above-described embodiments can be modified by one skilled in the art, especially in sizes and shapes and combination of various described features without departing from the scope of the invention. For example, it is contemplated that the plates for forming the microfluidic structure assembly can be made by direct micromachining a plate of suitable material to form the microgrooves, and the like, rather than by molding from a mold from by micromachining.

What is claimed is:

1. A microfluidic structure assembly, comprising:
   (a) a first plate including a plurality of microdepressions on a mating side of the first plate; and (b) a second plate including a plurality of microprojections on a mating side of the second plate, coupling to said plurality of microdepressions of the first plate such that at least some of the microprojections of one plate fit into at least some of the microdepressions of the other plate sufficiently far to lock the plates from sliding to form an assembly; wherein in the assembly at least one of the two plates comprising on its mating side microgrooves neighboring to microprojections and microdepressions, the microgrooves not being mated with any microprojections, such that the microgrooves of one plate are covered by the other plate to form microchannels, such that the assembly can be divided into a plurality of identical smaller assemblies each having one or more identical microchannels.

2. A microfluidic structure assembly, comprising:

(a) a first plate having a mating side and having on the mating side a plurality of microdepressions; and (b) a second plate having a mating side for coupling with the first plate's mating side, the second plate's mating side having a plurality of microprojections such that the microprojections of one plate fit into the microdepressions of the other plate sufficiently far to lock the two plates from sliding to form an assembly; wherein in the assembly at least one of the two plates comprising on its mating side one or more microgrooves neighboring microdepressions and microprojections, the microgrooves not mating with any mircroprojections, such that the microgrooves of one plate are covered by the other plate to form microchannels;

where in the microdepressions, microgrooves, and microchannels and are made by molding.

3. The assembly according to claim 2 wherein the microdepressions are smaller and shallower than and at least ten times as numerous as the microgrooves, and at least two of the microdepressions are nearer to the mid point than to an edge on the plate on which the microdepressions are located.

4. The assembly according to claim 2 wherein each plate comprises one or more microgrooves matching the microgrooves of the other plate to form microchanels in the assembly such that a microchannel has a cross section that is the sum of the cross sections of the two matching microgrooves.

5. The assembly according to claim 2 wherein the two coupled plates form a plurality of identical microchannels in the assembly such that the assembly can be divided to result in a plurality of identical pieces each including a microchannel.

6. The assembly according to claim 2 wherein the first and the second plate each comprises a plurality of microgrooves matching a plurality of microgrooves of the other plate to form microchannels in the assembly such that each of the microchannels has a cross section that is the sum of the cross sections of the two matching microgrooves, such that the assembly can be cut to result in a plurality of identical pieces each including a microchannel.

7. The assembly according to claim 6 wherein at least one plate further includes one or more cavities connected to the microchannels enabling fluid communication therewith, said cavities having a volume substantially larger than that of the microchannel.

8. The assembly according to claim 7 wherein the one or more cavities contain one or more chemicals for reacting with an analyte in a fluid to be passed through a microchannel to the one or more cavities.

9. The assembly according to claim 2 wherein the first plate and the second plate each comprises a plurality of microgrooves matching the microgrooves of the other plate to form microchannels in the assembly such that each microchannel has a cross section that is the sum of the cross sections of the two matching microgrooves, the microdepressions are smaller and shallower than and are at least ten times as numerous as the microgrooves, at least four of the microdepressions are nearer to a mid point than to an edge on the plate on which the microdepressions are located, the first and second plates are made of a thermoset polymer and are bonded together, such that the assembly can be cut to result in a plurality of identical pieces each including a microchannel.

10. The assembly according to claim 2 wherein each plate comprises both microprojections and microdepressions that mate with the microprojections and microdepressions of the other plate to lock the plates from sliding.

11. A method of making a microfluidic structure assembly, comprising:

(a) making a mold by micromachining one side of a substrate to form on the substrate a plurality of identical microridges and a plurality of microfingers, the microfingers having a height smaller than and at least ten times as numerous as the microridges, and at least ten of the microfingers are nearer to a mid point than to an edge on the mold on which the microfingers are located, at least some of the microfingers being positioned along the microridges proximate thereto;

(b) depositing on the mold a layer of liquid for forming a polymeric material to cover the microridges and cover said plurality of microfingers and allowing the liquid for forming a polymeric material to solidify to form a molded plate;

(c) releasing the molded plate from the mold such that the solidified plate has one or more microgrooves corresponding to the microridges on the mold, and a plurality of microdepressions corresponding to the microfingers, the molded plate being a first plate of an assembly;

(d) making a second molded plate to form a second plate of the assembly, the second plate including microgrooves mirroring the microgrooves of the first molded plate and microprojections positioned mirroring the positions of the microdepressions of the first plate, such that microdepressions of one molded plate correspond to microprojections of the other plate;

(e) bonding the two molded plates to form the assembly, said plurality of microdepressions and plurality of microprojections of the two plates coupling such that the microprojections of one plate fit sufficiently far into the microdepressions of the other plate to lock the plates from sliding such that the plates are proximate to each other for the microgrooves of the two plates to match to form microchannels for fluid flow; and (a) dividing the assembly with the first and second plates to result in a plurality of identical smaller assemblies each including a microchannel.

12. A method of making a mnicrofluidic structure assembly, comprising:

(a) making a first mold by micromachining one side of a first substrate to form on the first substrate a plurality of microholes;

(b) making a second mold by micromaching one side of the second substrate to form on the second substrate a plurality of microfingers with positions mirroring to the microholes of the first substrate;

(c) micromachining one or more microridges on at least one of the first substrate and the second substrate, the microridges not having positions mirroring to any microhole of another plate;

(d) depositing on the machined side of each mold a layer of liquid for forming a polymeric material to cover any machined microridges, microfingers and microholes, and allowing the liquid to solidify on each substrate to form a molded plate such that any microridge on the mold will form a microgroove on the molded plate, any microfinger will form a microdepression on the molded plate and any microhole will form a microprojection on the molded plate;

(e) releasing the molded plates from the molds; and (f) bonding a molded plate from the first substrate with a molded plate from the second substrate such that the two plates form an assembly, the microdepressions and the microprojections of the two plates are coupled by the microprojections of one plate fitting sufficiently far into the microdepressions of the other plate to lock from sliding, the plates are proximate to each other for the microgrooves to form microchannels for fluid flow.

13. The method according to claim 12 further comprising making the microdepressions to be smaller and shallower than and at least ten times as numerous as the microgrooves, and at least two of the microdepressions are nearer to a mid point than to an edge on the plate on which the microdepressions are located.

14. The method according to claim 12 further cormprising making one or more microgrooves on each plate to match one or more microgrooves on the other plate to form the microchannels such that a microchanmel has a cross section that is the sum of the cross sections of two matching microgrooves that face each other.

15. The method according to claim 12 further comprising making the first and second plates with a thermoset polymer and fastening them together by an adhesive.

16. The method according to claim 12 further comprising making the microdepressions of one plate adequately larger than the microprojections of the other plate such that pressing the two plates together will force excess adhesive into the microdepressions, and further comprising pressing the plates and curing the adhesive by heating.

17. The method according to claim 12 further comprising lapping a plate of the assembly on a side facing away from the microgrooves to obtain a flat surface on the plate.

18. The method according to claim 12 further comprising making the two plates of the assembly such that a plurality of identical microchannels are formed such that the assembly can be cut to result in a plurality of identical smaller assemblies each including a microchannel.

19. The method according to claim 18 further comprising dividing the assembly with the first and second plates to result in a plurality of identical smaller assemblies each including a microchannel.

20. The method according to claim 12 further comprising making microgrooves in each plate to match microgrooves of the other plate to form the microchannels such that a microchannel has a cross section that is the sum of the cross sections of the two matching microgrooves, making the microdepressions to be smaller and shallower than and at least ten times as numerous as the microgrooves, making the two plates of the assembly such that a plurality of identical microchannels are formed such that the assembly can be cut to result in a plurality of identical smaller assemblies, and dividing the assembly with the first and second plates to result in a plurality of identical smaller assemblies each including a microchannel.

21. The method according to claim 12 wherein both microdepressions and microprojections are made in each plate and microprojections on one plate are fitted into microdepressions of the other plate to align the two plates.

22. The method according to claim 12 further comprising depositing a release layer on the mold before depositing the liquid on the mold.

* * * * *